United States Patent [19]

van Wingerden

[11] Patent Number: Plant 7,263

[45] Date of Patent: Jul. 3, 1990

[54] CHRYSANTHEMUM NAMED C. P. HONEY GLOW

[75] Inventor: Jerry C. van Wingerden, Carpinteria, Calif.

[73] Assignee: California Plant Company, Carpinteria, Calif.

[21] Appl. No.: 362,081

[22] Filed: Jun. 5, 1989

[51] Int. Cl.[5] ..... A01H 5/00

[52] U.S. Cl. ..... Plt./79

[58] Field of Search ..... Plt./79

*Primary Examiner*—James R. Feyrer

*Attorney, Agent, or Firm*—Charles W. Rummler

[57] ABSTRACT

A new Chrysanthemum variety of the genus Morifolium, Ramat, particularly adapted for greenhouse culture with a nine-week response for recurrent, year-round, profuse d production of relatively small, button-shaped, long-lasting flowers of a spicy, golden bronze coloration. The plant itself has a strong, upright growth habit with ample amount of foliage reaching an average height of about 80 to 85 cm. and is particularly suited for greenhouse culture under normal Chrysanthemum growing procedures.

1 Drawing Sheet

BACKGROUND OF THE NEW PLANT

This new variety of Chrysanthemum was discovered by me as a sport of the unpatented variety Climax being grown in greenhouse at Westland Floral Nursery at Carpinteria, Calif. and was particularly noticed by me because of the golden bronze coloration of its flowers contrasting with the light purple pink coloration of the parent variety and because of its striking color, I propagated this sport by means of cuttings at Westland Floral Nursery with such satisfactory results that I propagated this new variety through several successive generations which demonstrated clearly that its novel characteristics would hold true from generation to generation and appeared to be firmly fixed.

DESCRIPTION OF THE DRAWING

My new Chrysanthemum variety is illustrated by the accompanying full-color photographic drawings which, in the upper view, shows a cluster of the blooms illustrating the striking nature of their color, and in the lower view shows a close-up of several blooms and the particular manner in which the central portion of each bloom is highlighted by the light yellow coloration of the reverse side of the more or less upright petals of the central portion of the flower, the color characteristics of the flowers being shown as nearly true to those herein specified as is reasonably possible to obtain by conventional photographic procedures.

DESCRIPTION OF THE NEW PLANT

The following is a detailed description of my variety of chrysanthemum plant with the color designations according to The R.H.S. Colour Chart published by The Royal Horticultural Society of London, England.

THE PLANT

Origin: Sport.

Parentage: The chrysanthemum variety Climax (unpatented).

Classification:

*Botanic.*—Chrysanthemum Morifolium, Ramat.

*Commercial.*—Greenhouse Chrysanthemum.

Form: Upright herbaceous perennial.

Height: Averaging about 80 to 85 cm.

Growth: Sturdy and upright with good strength.

Growth rate: Rapid.

Branching character: Good when pinched.

Response: Nine weeks.

Foliage:

*Quantity.*—Moderate.

*Leaflets.*—Number: Typically, about 20. Size: Medium. Shape: Oblong and lobed with entire margins and pointed tipped lobes. Texture: Generally smooth with slight pubescence. Color: Upper side — 147A. Under side — 147B.

*Stipules.*—Number: Two for each leaf. Size: About 3 to 5 mm.

THE BUD

Form:

*When opening.*—Cup shaped.

Size:

*Diameter.*—About 1 to 1.5 cm.

*Length.*—About 0.8 to 1.2 cm.

Rate of opening: Moderate.

Color of petals:

*When sepals first divide.*—Canary yellow, RHS-9D with distal tips of Aureolin, RHS-12A.

*When petals begin to unfurl.*—163A inside and 162B on the reverse side.

Sepals:

*Number:*—Approximately twenty.

*Shape.*—Spear shaped.

*Character.*—Hooded over the bud before dividing and curled back when flowers open.

*Color.*—Both inside and outside — Light green, 138A/B.

Calyx:

*Shape.*—Funnel-shaped.

*Size.*—Moderate.

*Splitting.*—Calyx does split.

*Aspect.*—Slightly pubescent.

Peduncle:

*Length.*—From 15 to 35 cm.

*Character.*—Rigid, strong and upright.

*Color.*—146B.

THE FLOWER

Blooming habit: Recurrent and profusely, with controlled photoperiod.
Natural blooming period: Fall.
Size of bloom: Relatively small.
*Diameter.*—About 4 to 5 cm.
*Depth.*—About 1 to 1.5 cm.
Borne: Singly, as part of a spray.
Shape:
*When bloom first opens.*—Cup-shaped.
*When bloom matures.*—Dome-shaped.
Petals:
*Number of ray florets.*—About 210 to 230.
*Arrangement.*—Whorled on the receptacle to produce a button form.
*Shape.*—Generally, long spatulate with entire margins.
*Texture.*—Soft.
*Aspect.* Velvety.
*Color.*—Upper side — Greyed orange, 170A/B. Base—Citron green, 151B. Reverse side and edges of upper side — Very pale yellow, 13D.
Discoloration after full bloom: Slightly faded.
Persistence: The flower hangs on persistently.
Fragrance: Typical for Chrysanthemum.
Lasting quality: Excellent, both on the plant and as cut flower.

THE REPRODUCTIVE ORGANS

Stamens: None.
Pistils:
*Number.*—210 to 230.
*Styles.*—Length: About 2 mm. Color: 154A.
*Stigmas.*—Color: 154B.
Character of the ovaries: Tiny, oval shaped and white in color.

In general, this new variety of Chrysanthemum most nearly resembles the variety Climax (unpatented) and the following chart illustrates the principal distinctions of the two plants, the chart being based on comparative flowering at Westland Floral made in November 1988 at Carpinteria, Calif. In general, the variety Climax is a light pink button, whereas C.P. Honey Glow is a spicy golden brown and holds its color exceptionally well.

| Petalage | C.P. Honey Glow | Climax |
|---|---|---|
| Ray Florets | 210–230 | 210–220 |
| Body Color | 170A/B | 78C |
| Base Color | 151B | 151A |
| Reverse Color | 13D | 76D |

I claim:

1. The new and distinct variety of *Chrysanthemum morifolium,* substantially as herein shown and described, particularly characterized by the spicy golden bronze coloration of its relatively small button-shaped blooms in which the florets at the more or less central portion of the flower are generally upright so as to display the bright yellow coloration of their underside thereby brightening the bronze coloration of the florets forming the major portion of the flower body.

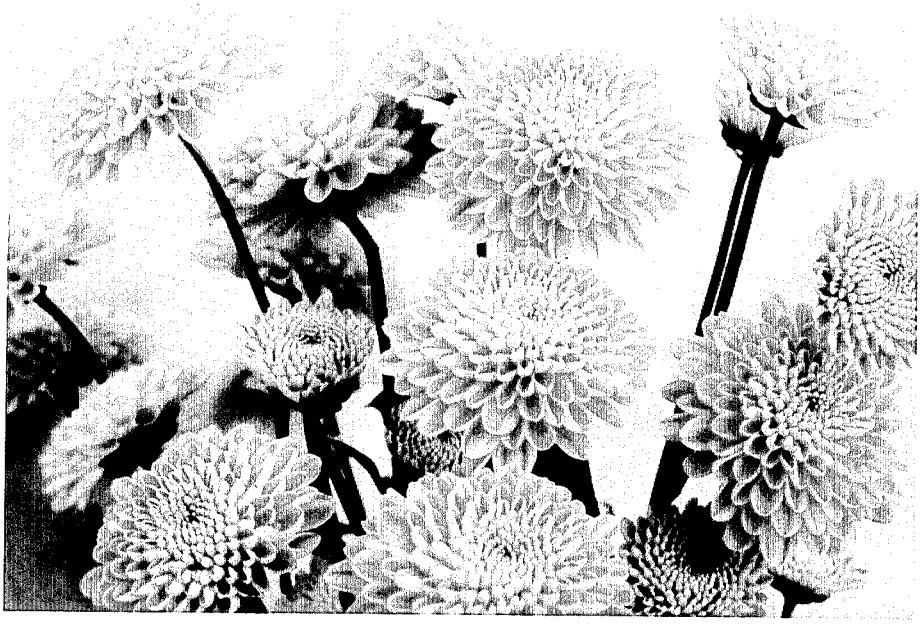
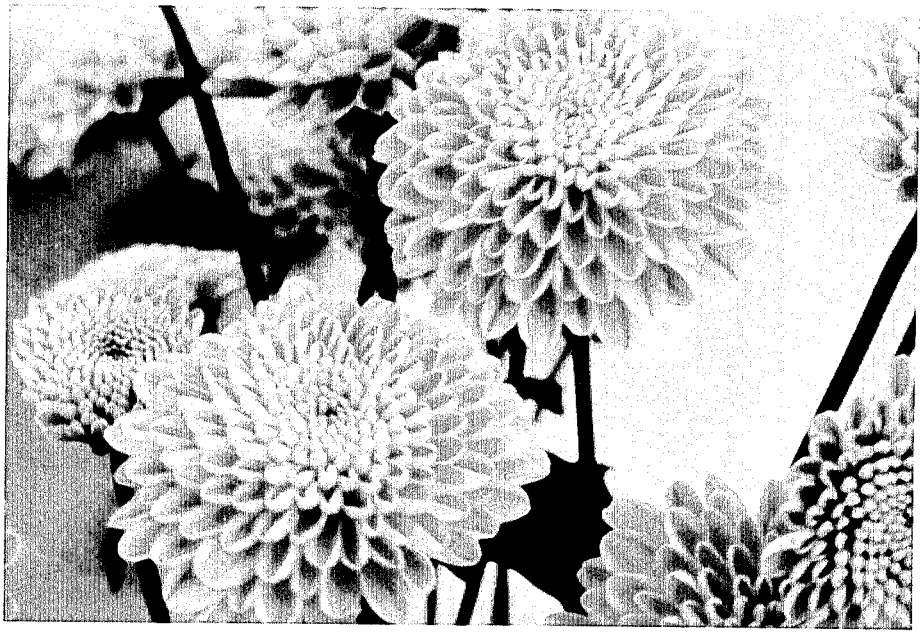

* * * * *